United States Patent [19]
Fenstermaker

[11] 4,370,150
[45] Jan. 25, 1983

[54] ENGINE PERFORMANCE OPERATING ON FIELD GAS AS ENGINE FUEL

[75] Inventor: Roger W. Fenstermaker, Bartlesville, Okla.

[73] Assignee: Phillips Petroleum Company, Bartlesville, Okla.

[21] Appl. No.: 292,102

[22] Filed: Aug. 11, 1981

Related U.S. Application Data

[63] Continuation-in-part of Ser. No. 180,172, Aug. 21, 1980, abandoned.

[51] Int. Cl.$^3$ .............................................. B01D 53/32
[52] U.S. Cl. ........................................... 55/16; 55/73
[58] Field of Search ............................. 55/16, 73, 158

[56] References Cited

U.S. PATENT DOCUMENTS

| | | | |
|---|---|---|---|
| 2,159,434 | 5/1939 | Frey | 55/16 X |
| 2,699,836 | 1/1955 | Barton, Jr. | 55/16 |
| 2,843,555 | 7/1958 | Berridge | 528/901 X |
| 2,966,235 | 12/1960 | Kammermeyer | 55/16 |
| 3,189,662 | 6/1965 | Vaughn, Jr. | 260/824 |
| 3,256,675 | 6/1966 | Robb | 55/16 |
| 3,396,510 | 8/1968 | Ward et al. | 55/16 |
| 3,534,528 | 10/1970 | Porter | 55/16 |
| 3,616,607 | 11/1971 | Klass et al. | 55/16 |
| 3,674,435 | 7/1972 | Van Luik, Jr. et al. | 55/16 X |
| 4,011,299 | 3/1977 | Henis et al. | 423/239 |
| 4,028,069 | 6/1977 | Nolley, Jr. et al. | 55/62 X |
| 4,130,403 | 12/1978 | Cooley et al. | 55/16 |
| 4,147,754 | 4/1979 | Ward | 55/16 X |
| 4,181,675 | 1/1980 | Makin et al. | 55/16 X |
| 4,230,463 | 10/1980 | Henis et al. | 55/16 |

FOREIGN PATENT DOCUMENTS 1062176  9/1979  Canada .................................. 55/16

OTHER PUBLICATIONS

Perry, Chemical Engineers' Handbook, 5th Edition, 1973, pp. 6-29 to 6-32 and 24-30 to 24-36.
General Electric Technical Information Bulletin, Browall et al., "Permselective Membranes for Oxygen Enrichment", 5/1976, 4 pp.
General Electric Permselective Membranes, Membrane Products, pp. 3 to 11.
Kobe, Advances in Petroleum Chemistry & Refining, vol. 6, 1962, pp. 77 to 79.
Baumeister, Mechanical Engineers' Handbook, 1958, pp. 14-42 to 14-43 and 9-99 to 9-102.
Encyclopedia of Polymer Science & Technology, vol. 12, 1970, pp. 531-543 and 545-552.
C & EN, 5/12/1979, "Science/Technology Concentrates", p. 13.
Ward III et al., J. of Membrane Science, 1(1976) 99-108, "Ultrathin Silicone/Polycarbonate Membranes for Gas Separation Processes".
Polymer Letters, vol. 7, pp. 569-572 (1969), "The Synthesis & Properties of Alternating Block Polymers of Dimethysiloxanes Bis-phenol-a Carbonate".
DE3016305 Abstr. J: Chem. Engr.
ZA7904933 Abstr. J: Chem. Engr.
Monsanto Prism Separator Booklet, "Simple Separation Systems for Hydrogen Recovery".
Chem. & Engr. News, May 19, 1980, pp. 57, 58, 60.
Chem. & Engr. News, Nov. 19, 1979, pp. 6 & 7.
Chem. Processing, Jan. 1981, pp. 30, 31.
Chem. Abstracts 94:48298w (1981).
Separation Science and Technology 15(IV) pp. 1059-1068 (1980) Henis et al.
Hydrocarbon Processing, May, 1980, pp. 115-118.

*Primary Examiner*—Robert H. Spitzer

[57] ABSTRACT

Natural gas is improved for use as an engine fuel gas stream by treating with a membrane through which hydrogen sulfide and heavier hydrocarbons permeate preferentially. The reject gas is returned to the natural gas pipeline. The upgraded gas is used for engine fuel to operate the pipeline compressor. Treatment of the natural gas provides a cleaner, higher octane fuel for engine use, and reduces engine wear and failure.

9 Claims, 5 Drawing Figures

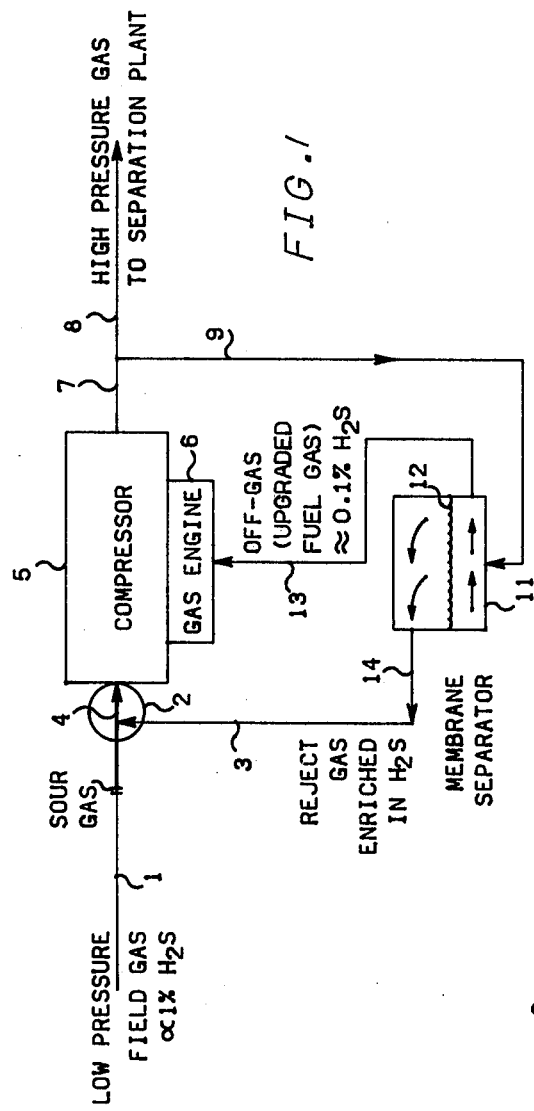
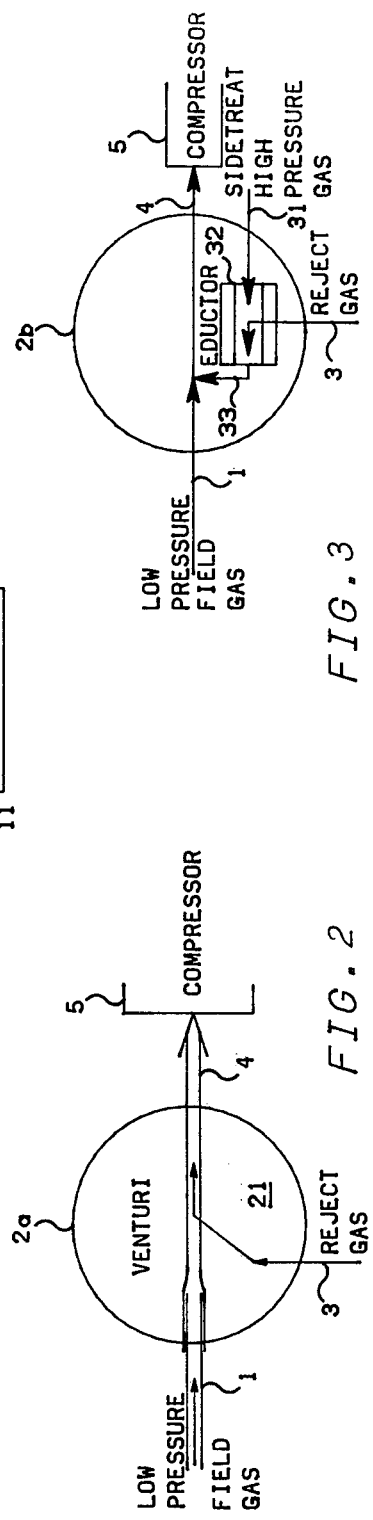
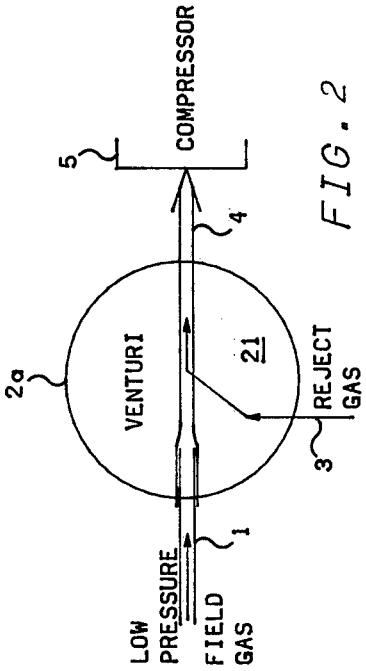

ENGINE PERFORMANCE OPERATING ON FIELD GAS AS ENGINE FUEL

This is a continuation-in-part application of copending application Ser. No. 180,172 filed Aug. 21, 1980, now abandoned.

FIELD OF THE INVENTION

The invention relates to the use of field gas as fuel gas for compressor station engines. In another aspect, the invention pertains to methods to protect engines employing natural gas as fuel from corrosion and wear due to hydrogen sulfide-containing fuels. In a further aspect, the invention pertains to methods to upgrade the octane rating of field natural gas.

BACKGROUND OF THE INVENTION

Field compressor stations for natural gas gathering commonly employ engines designed to operate on methane, the primary constituent of natural gas. However, such engines often are not adequately designed for the use of raw or field gas. Problems of engine wear and failure attributable to corrosion from the frequently high hydrogen sulfide content of the raw field natural gas have been increasing. As wells go ever deeper, sulfur-containing gases appear more frequently. At the same time, some gas fields which have not been produced due to the undesirable content of hydrogen sulfide now are coming into production. As fields mature which heretofore have had naturally high pressures requiring little or no compression for pipeline usage, the pressures tend to decline down to the point where field compressors are required. Thus, for many reasons, increasing numbers of compressors come in use. Unfortunately, the engine failure rate also is accelerating.

Another problem encountered with the use of field gas frequently involves relatively low octane rating of such gases, primarily attributable to the significant amounts of higher hydrocarbons such as $C_2$–$C_7$ (ethane, propane, butane, pentane, hexane, etc.) in the natural gas stream. These adversely affect (lower) the octane rating of the field gas as a fuel.

Needed has been a method to process the field natural gas on the spot, providing an upgraded fuel gas in such quantities as needed for the engine, and recycling reject gas back into the pipeline. The installation preferably should be simple, capable of operating substantially unattended, and be energy-effective in not placing an added energy-consuming burden on the pumping station.

BRIEF DESCRIPTION OF THE INVENTION

I have discovered a method of upgrading a raw field natural gas stream containing hydrogen sulfide and/or higher normally gaseous hydrocarbons to improve the quality of a portion of the field gas as an engine fuel gas while cycling the reject portion back into the gas pipeline. The method is energy-conscious in that it operates unattended, with no moving parts, and no waste. Stream gas components not utilized for engine fuel gas are recycled back to the pipeline.

In accordance with my invention, a side gas draw-stream, taken from a high pressure gas stream on the discharge side of a gas compressor, is applied to a semi-permeable membrane unit. This membrane is permeable, and selective, such that hydrogen sulfide and the larger molecules of the higher gaseous hydrocarbons tend preferentially to pass through the membrane. The improved upgraded off-gas stream which does not pass the membrane is utilized, as needed, for fuel gas in the gas engine. The reject gas stream, enriched in hydrogen sulfide and/or in higher hydrocarbons, is passed back to the compressor via the lower pressure side of the gas compressor.

Suitable membranes include silicone membranes, such as those prepared from dialkylsilicones or the silicone-polycarbonates; and the multicomponent membranes described in U.S. Pat. No. 4,230,463.

My invention provides a nonwaste solution to a vexing problem in that no components are wasted, and no components are discharged to the atmosphere. All components are either utilized as engine fuel gas, or simply put back into the pipeline. My invention is operational within widely operating ranges since the gas engine simply "draws" on the stream as needed and no mechanical regulation is needed. Return of the reject gas into the low pressure side of the gas compressor line can be by various means such as a venturi, eductor (ejector), or other as desired.

BRIEF DESCRIPTION OF THE DRAWINGS

FIG. 1 shows the overall scheme of my process. A low pressure field gas or sour gas 1 is mixed 2 with reject gas 3 and fed 4 to gas compressor 5 operated as necessary by gas engine 6. Gas compressor 5 produces a high pressure compressed gas stream 7 which can be fed to a gathering transmission system 8 or separation plant as desired. A small side high-pressure gas stream 9 is taken to membrane separator 11.

Figure 4:
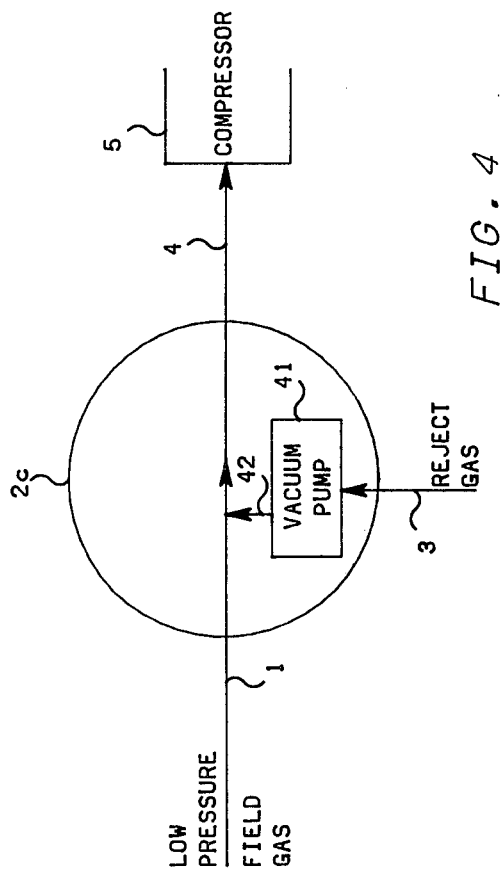

Membrane separator 11 contains a membrane 12 which is permeable and selective so that hydrogen sulfide and/or higher molecular weight hydrocarbons (ethane through hexane) normally contained in a field gas preferentially pass therethrough to form a reject 14, 3 gas stream enriched in hydrogen sulfide and/or higher hydrocarbons, leaving now-upgraded off-gas 13 for fuel gas usage. The thus-upgraded fuel gas that does not pass through the membrane 12 forms as off-gas 13 which is utilized in the gas engine 6 as upgraded fuel gas as the engine needs it. Reject gas 14 is returned 3 to the low pressure side of the compressor system by means indicated generally by the circle 2 in the sour gas line, and as shown in more detail in several options 2a, 2b, and 2c shown respectively in FIGS. 2, 3, and 4. As can be realized, the volume of gas in the main line 1, 8 is so large compared to the small recycle 14, that no significant difference in main stream quality occurs.

FIG. 2 illustrates one of several means which can be utilized in returning the reject gas stream 3 into the main line 1, 4. Here, reject gas 3 is returned to low pressure field gas line 1 by means of venturi 21 to produce the mixed gas feed 4 to compressor 5.

FIG. 3 illustrates another return method which can be utilized. A side stream high-pressure gas line 31, taken from take-off stream 9 or from the high-pressure discharge 7 of compressor 5, is passed through eductor 32 to pull in the reject gas stream 3 to form a mixed gas 33 feed into the low pressure field gas line 1 to form mixed stream 4 to compressor 5.

FIG. 4 illustrates still another method of return which can be utilized. A vacuum pump 41 takes the reject gas stream 3 to form a return stream 42 back to low pressure fuel gas line 1 to form the mixed feed 4 to compressor 5. The vacuum pump can operate off the compressor engine 6, or separately if desired.

Figure 5:
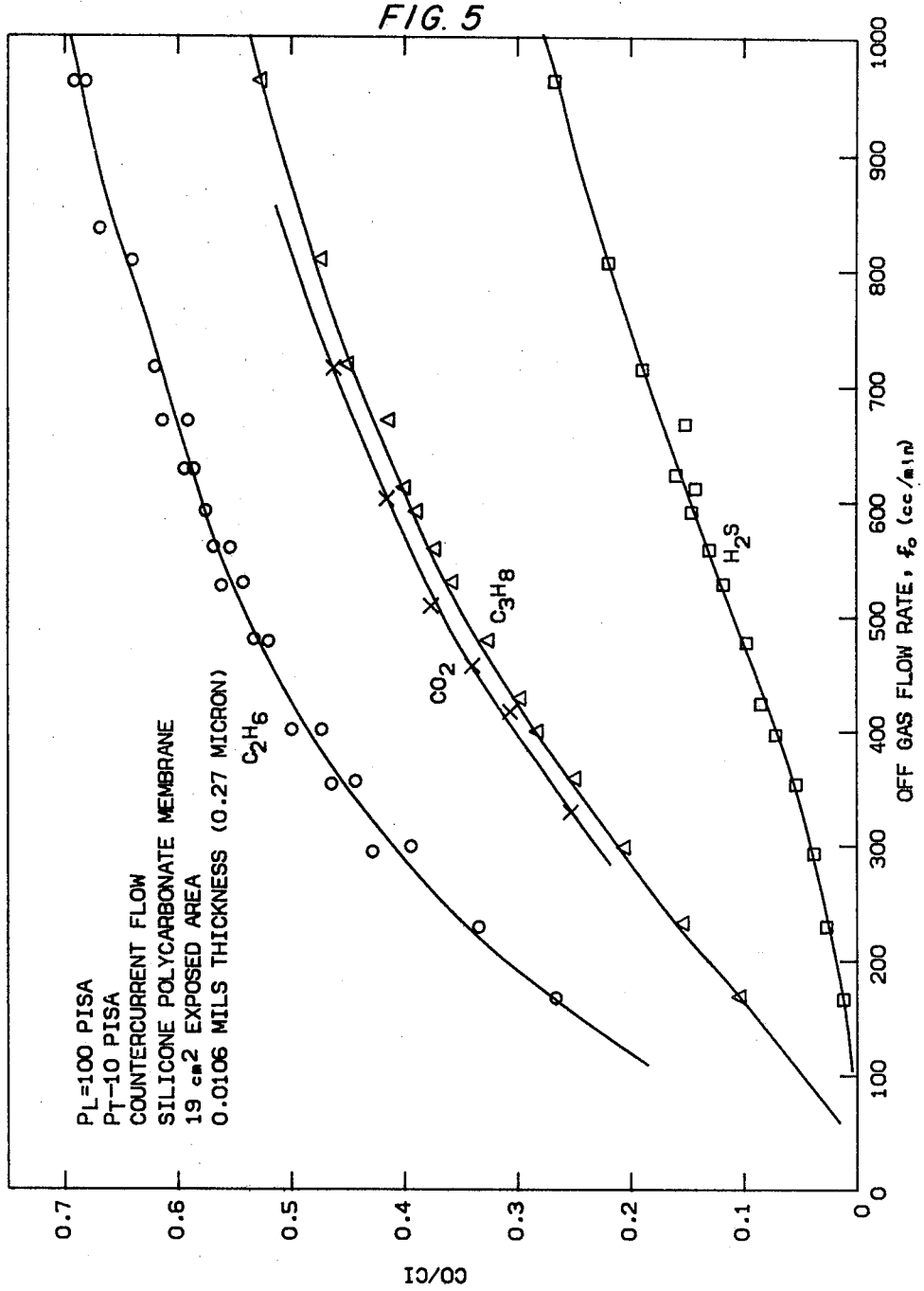

FIG. 5 illustrates the reduction in concentration in the off-gas of those minor components that are more permeable through a silicone-polycarbonate membrane than H$_2$S, plotted versus off-gas flow rate. ($C_o$ is the concentration of a particular species in the off-gas, and $C_i$ is its concentration in the inlet gas). In the figure, the ratios of $C_o/C_i$ for C$_2$H$_6$, CO$_2$, C$_3$H$_8$, and H$_2$S are plotted versus total off-gas flow rate $f_o$ in cc/min. The inlet gas pressure and the off-gas pressure are 100 psia; the reject gas pressure is 10 psia. The membrane is a commercial silicone-polycarbonate membrane (GE MEM-213), 0.27 micron (0.0106 mil) thick and 19 cm$^2$ in area. The reject gas is extracted in a direction countercurrent to the flow of the inlet gas. These relationships while considered typical, will vary with pressures, temperatures, flow rates, method of through-gas extraction, type of membrane, and other factors.

DETAILED DESCRIPTION OF THE INVENTION

Low pressure field gas, containing primarily methane, with hydrogen sulfide and/or normally gaseous higher hydrocarbons of about the range of C$_2$–C$_6$ carbon atoms per molecule, is compressed to produce a high pressure gas for pipeline transmission or to a separation plant. A small portion of the high pressure compressed field gas flow is taken as fuel gas to use in a natural gas engine driving the compressor.

In accordance with my invention, a side-draw or take-off stream of the high pressure gas is applied to a semi-permeable membrane unit. The unit contains a semi-permeable membrane selected for and characterized such that hydrogen sulfide and/or higher normally gaseous hydrocarbons pass through the membrane to form a reject gas stream. The reject gas stream is returned to the field gas stream at the suction side of the compressor. This treatment leaves an upgraded fuel gas substantially depleted in hydrogen sulfide and substantially depleted in the higher hydrocarbons. The upgraded fuel gas then is utilized as fuel gas for the gas engine. This process provides corrosion protection for the gas engine, and at the same time provides an upgraded fuel gas with improved (higher) anti-knock properties.

Exemplarily, a raw low-pressure field gas typically produced at such as about 9 psia frequently contains on the order of about 1 to 2 mole % hydrogen sulfide, and typically such as about 7% ethane, 3% propanes, 2% butanes, 1% pentanes, and 0.5% hexanes. Of course, these amounts and ratios can and do vary widely from one gas-producing field to another, and even within a field. Compression typically produces a high pressure gas stream, such as at about 133 psia and at a temperature of usually about 30° F. above ambient. By my invention, from the high pressure stream is taken a side stream of such as, for example, about 4% by volume of the total flow which side stream is applied to the membrane unit. The amount taken, of course, can vary widely depending on mainstream flow, fuel needs of the compressor, and the like. The membrane, semi-permeable and selective toward the undesirable components, produces an off-gas stream for compressor engine fuel of such as about 0.1 mole % hydrogen sulfide and about 89% methane, 4% ethane, 1% propanes, and 0.5% butanes and other higher hydrocarbons present. The small stream of reject gas which has passed through the membrane, now enriched in hydrogen sulfide and/or enriched in the higher hydrocarbons, is reinjected into the intake low pressure side of the compressor.

Efficiency of the process scheme is dependent to some extent on the relative size and basic type of the membrane versus demand rate from the engine, as well as the method chosen of applying the gas to the membrane relative to method of removal of the reject gas: cocurrent, countercurrent, by pump, or the like. The system is capable of simultaneous removal from the gas stream of such as about 90% of the hydrogen sulfide to reduce the otherwise potential corrosion problems, together with concurrent removal of between about 40 and 95% of C$_2$–C$_7$ hydrocarbons to thus raise the octane of the fuel gas and minimize knock in the engine.

MEMBRANE

The membrane employed is one which has the property of very high permeability for some molecules. The high permeability is toward hydrogen sulfide and higher hydrocarbons. Correspondingly a low or very low permeability toward methane. Types of suitable such membranes are the silicone membranes, either dialkylsilicones, or silicone-polycarbonates, and the multi-component membranes described in U.S. Pat. No. 4,230,463.

The silicone membranes presently are preferred since they exhibit high separation factors for many gases, i.e., high ratio of permeabilities. These silicone membranes can be of the silicone rubbers which are dialkylsilicones, or of the silicone-polycarbonate type.

The types of silicone rubbers, the dialkylsilicones as described in U.S. Pat. No. 2,966,235, hereby incorporated by reference, are among those suitable for use as membranes in the process of my invention. These include the homopolymeric dialkylsiloxanes and copolymers of dialkylsiloxane and siloxanes of the type RR'SiO where R is a monocyclic aryl radical and R' is alkyl or monocyclic aryl. The alkyl group is preferably methyl. Among the most common silicone rubbers are the polymers chemically defined as dimethyl polysiloxane having the formula [(CH$_3$)$_2$SiO]$_n$ where n is an integer above 500 and wherein the polymer has the characteristics of curing into a solid, rubber-like material having an average molecular weight of as high as 500,000 or more.

Such silicone rubbers conventionally are manufactured by condensation of dialkylsilanediol such as dimethylsilanediol:

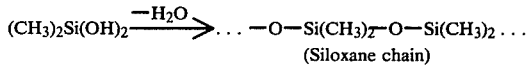

(Siloxane chain)

Suitable silicone-polycarbonate copolymer membranes have the general structure

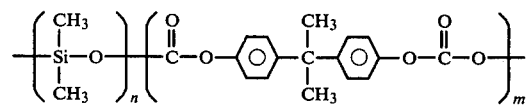

where —CH$_3$ can alternatively be any lower alkyl as described above. See U.S. Pat. No. 3,189,662, incorporated herein by reference, for disclosure of preparation of such copolymers.

The use of the semi-permeable selective-permeability membranes should not necessarily imply the passage of one gas to the complete exclusion of other gases. Rather, it indicates the difference in the flow rate of the molecular species present through the permeable membrane. The result always is that a gas mixture on the high pressure side of the membrane is depleted in concentration of the more permeable component or components just as the gas mixture on the low pressure side of the membrane is enriched in the more permeable component or components.

It is believed, though I do not wish to be bound by theories, that a gas dissolves in the membrane on the side having a high partial pressure, diffuses through the membrane under the influence of the pressure difference, then comes out of solution on the low pressure side.

Dialkyl Silicone Membranes

Presently convenient for availability and economy are the dialkyl silicone membranes, such as dimethyl silicone membranes. The membranes should be free of pin holes, yet sufficiently thin, such as about 0.001 to 1 mil, preferably about 0.001 to 0.01 mil, presently preferred about 0.005 to 0.01 mil, to allow quantities of gas having practical significance to pass through the membranes.

The silicone membranes can be employed unbacked, backed on one side, or backed on two sides, depending on the square footage area to be exposed to the gas, and depending on requirements for strength and durability, depending on the particular membrane employed. Backings can be of any convenient high strength chemically resistant material to improve general durability and avoid rupture by mechanical or accidental abrasion.

Relative Permeabilities of Various Silicone Membrane Types

Presently very useful membranes are available from General Electric Company (G.E.) as a "Dimethyl Silicone" membrane, and "MEM-213" Silicone-Polycarbonate Copolymer membrane.

Comparison of typical membrane properties can be observed from data shown in Table I:

TABLE I

|  | Membrane Type | |
|---|---|---|
|  | Dimethyl Silicone* | Silicone-Polycarbonate** |
| Tensile strength (psi) room temp. 400° F. | 500–1800 400 | 2600 — |
| Specific gravity of base elastomer | 1.1–1.2 | 1.0–1.1 |
| Tear resistance lbs./inch at room temperature (ASTM D624-DieB) | 200 Notch parallel to 314 roll direction | |
| Service life at 200° F. in dry Autoclave at | Notch perpendicular to roll direction 414 continuous 275° F. | continuous 250° F. |
| Heat sealable | no | yes |
| Dielectric constant (60 cps) | 1.78 | 1.83 |
| Dielectric strength (volts/mil) | 2200 | 7000 |
| Volume resistivity (ohm-cm) | $8.5 \times 10^{14}$ | $1.8 \times 10^{15}$ |
| Resistance to water | excellent | excellent |
| Transparency | translucent | clear |
| Permeability to bacteria | impermeable | impermeable |

*G.E. dimethyl silicone
**G.E. silicone polycarbonate

Relative gas permeabilities for two types of membranes are shown in Table II:

TABLE II

| Selected Gas Permeabilities[a] | | |
|---|---|---|
|  | Membranes | |
| Gas | Dimethyl Silicone | Silicone-Polycarbonate[b] |
| $H_2$ | 55[c] | 21[c] |
| He | 30 | |
| $NH_3$ | 500 | |
| $H_2O$ | 3000 | |
| CO | 30 | |
| $N_2$ | 25 | 7 |
| NO | 50 | |
| $O_2$ | 50 | 16 |
| $H_2S$ | 840 | |
| Ar | 50 | |
| $CO_2$ | 270 | 97 |
| $N_2O$ | 365 | |
| $NO_2$ | 635 | |
| $SO_2$ | 1250 | |
| $CS_2$ | 7500 | |
| $CH_4$ | 80 | |
| $C_2H_6$ | 210 | |
| $C_2H_4$ | 115 | |
| $C_2H_2$ | 2200 | |
| $C_3H_8$ | 340 | |
| $n-C_4H_{10}$ | 750 | |
| $n-C_5H_{12}$ | 1670 | |
| $n-C_6H_{14}$ | 785 | |
| $n-C_8H_{18}$ | 715 | |
| $n-C_{10}H_{22}$ | 360 | |
| HCHO | 925 | |
| $CH_3OH$ | 1160 | |
| $COCl_2$ | 1250 | |
| Acetone | 490 | |
| Pyridine | 1595 | |
| Benzene | 900 | |
| Phenol | 1750 | |
| Toluene | 760 | |
| Xe | 171 | |
| $CCl_4$ | 5835 | |
| $CH_2O$ | 925 | |
| $C_2H_2$ | 2200 | |
| Freon 11 | 1290 | |
| Freon 12 | 107 | |
| Freon 22 | 382 | |
| Freon 114 | 211 | |
| Freon 115 | 51 | |

[a]Units are $10^{-9} \dfrac{\text{cc gas (RTP*)} \cdot \text{cm thick}}{\text{sec} \cdot \text{cm}^2 \cdot \text{cmHg}\Delta P}$

*RTP = Room temperature and pressure, i.e. presumably no effort was made when measuring these permeabilities to correct to STP.
[b]The silicone polycarbonate membrane values given are stated by G.E. to be representative permeabilities approximately one-third to one-half those for dimethyl silicone membrane. Assuming the relative permeabilities remain the same between the two types of membranes, the respective permeabilities for the silicone polycarbonate films can be estimated from the data given above for the other gases shown.
[c]The above figures of permeabilities all are taken from G.E. literature.

Factors Affecting Determination of Membrane Area

Factors affecting the area of membrane to be used for gas purification in a specific installation include the extent of $H_2S$ reduction and/or $C_2$–$C_7$ reduction desired, the inlet gas pressure, the inlet gas concentrations of other undesirable components and their relative permeabilities, membrane thickness, reject gas pressure, and method of reject gas extraction.

The larger the area of membrane used, the lower the residual $H_2S$ and/or $C_2$–$C_7$ hydrocarbon concentrations in the off-gas, in general.

The higher the concentration of hydrogen sulfide and/or other undesirable components, the larger should be the membrane area.

The higher the pressure of the inlet gas to the membrane unit relative to the pressure of the reject gas from the membrane unit, the greater will be the efficiency of separation, i.e, the cleaner will be the off-gas to the engine.

The reject gas pressure and flow rate on the membrane, of course, affect the separation.

In the following Table III, $f_o$ represents the flow rate of upgraded gas of 90% H$_2$S reduction at inlet pressure $P_i$ at 96 psia, and at various values of pressure $P_t$ on the reject gas side of the membrane. These data are for a silicone-polycarbonate membrane area of 119 cm$^2$ of a membrane thickness of 18 micron (0.7 mil) employing a G.E. MEM-213 (silicone-polycarbonate) membrane:

TABLE III

EFFECT OF REJECT GAS PRESSURE ON SILICONE-POLYCARBONATE MEMBRANE PERFORMANCE

| $P_i$(psia) | $P_t$(psia) | $f_o$, Flow Rate of Upgraded Gas Observed (cc/min) |
|---|---|---|
| 96 | (0) | *(78) |
| 96 | 0.04 | 78 |
| 96 | 3.6 | 55.5 |
| 96 | 7.2 | 40 |
| 96 | 14.2 | 29.5 |
| 96 | (96) | (0) |

*the ( ) indicates limiting cases not actually run.

Note that allowing $P_t$ to go from 0 to 96 psia caused the flow rate of upgraded gas to go from 78 cc/min to 0. Obviously, a larger flow for a given size membrane implies less membrane will be needed in a field unit for cleaning up the field gas. Note also that when reject-side pressure $P_t$ went from 0 to 14.4 psia (a loss in total pressure differential of only 15%) the performance of the system decreased by 64%. Obviously, $P_t$ is an important critical parameter in specifying a field unit.

The method of reject gas extraction or removal from the membrane unit affects membrane area sizing and separation results. Contact and withdrawal can be cocurrent, i.e., reject gas flow being in the same direction as the inlet gas flow. Contact and takeoff can be countercurrent, with gas applied to one side and taken off to the other side in opposite directions. Alternatively, relative gas flow can be cross-current with through-gas flow perpendicular to inlet gas flow.

The countercurrent mode of reject gas extraction presently seems to be the most efficient. This can be observed by utilizing as exemplary a 65 cubic feet per minute flow with 90% hydrogen sulfide reduction and applied pressure $P_i$ of 100 psia, employing a silicone polycarbonate membrane (G.E. MEM-213) 0.27 microns thick with results shown in Table IV:

TABLE IV

| | Effect of Throughgas Withdrawal Method on Required Silicone-Polycarbonate Membrane Area | |
|---|---|---|
| $P_t$(psia) | Cocurrent | Countercurrent |
| 0.2 | 50 ft$^2$ | 50 ft$^2$ |
| 10.0 | 420–470 ft$^2$ | 80 ft$^2$ |
| 15.0 | * | 105 ft$^2$ |
| 25.0 | * | 185 ft$^2$ |

*Could not get 90% reduction

Multi-Component Membranes

The multi-component membranes, useful in my invention in purifying field gas for use in gas engines, are described in detail in U.S. Pat. No. 4,230,463, incorporated herein in total by reference.

Briefly, the multicomponent membranes for gas separation, according to the invention, can be films or hollow filaments, or fibers, having a porous separation membrane, or substrate, and a coating in occluding contact with the porous separation membrane.

The material used for the separation membrane may be a solid natural or synthetic substance having useful gas separation properties. In the case of polymers, both addition and condensation polymers which can be cast, extruded or otherwise fabricated to provide separation membranes are included. The separation membranes can be prepared in form, for example, by casting from a solution comprised of a good solvent for the polymeric material into a poor or nonsolvent for the material. The spinning and/or casting conditions and/or treatments subsequent to the initial formation, and the like, can influence the porosity and resistance to gas flow of the separation membrane.

Generally organic or organic polymers mixed with inorganics are used to prepare the separation membrane. Typical polymers suitable for the separation membrane according to the invention can be substituted or unsubstituted polymers and may be selected from polysulfones; poly(styrenes), including styrene-containing copolymers such as acrylonitrilestyrene copolymers, styrene-butadiene copolymers and styrene-vinylbenzylhalide copolymers; polycarbonates; cellulosic polymers, such as cellulose acetate-butyrate, cellulose propionate, ethyl cellulose, methyl cellulose, nitrocellulose, etc.; polyamides and polyimides, including aryl polyamides and aryl polyimides; polyether; poly(arylene oxides) such as poly(phenylene oxide) and poly(xylene oxide); poly(esteramide-diisocyanate); polyurethanes; polyesters (including polyarylates), such as poly(ethylene terephthalate), poly(alkyl methacrylates), poly(acrylates), poly(phenylene terephthalate), etc.; polysulfides; polymers from monomers having alpha-olefinic unsaturation other than mentioned above such as poly(ethylene), poly(propylene), poly(butene-1), poly(4-methyl pentene-1), polyvinyls, e.g., poly(vinyl chloride), poly(vinyl fluoride), poly(vinyl alcohol), poly(vinyl esters) such as poly(vinyl acetate) and poly(vinyl propionate), poly(vinyl pyridines), poly(vinyl pyrrolidones), poly(vinyl ethers), poly(vinyl ketones), poly(vinyl aldehydes) such as poly(vinyl formal) and poly(vinyl butyral), poly(vinyl amides), poly(vinyl amines), poly(vinyl urethanes), poly(vinyl ureas), poly(vinyl phosphates), and poly(vinyl sulfates); polyallyls; poly(benzobenzimidazole); polyhydrazides; polyoxadiazoles; polytriazoles; poly(benzimidazole); polycarbodiimides; polyphosphazines; etc., and interpolymers, including block interpolymers containing repeating units from the above such as terpolymers of acrylonitrile-vinyl bromide-sodium salt of para-sulfophenylmethallyl ethers; and grafts and blends containing any of the foregoing. Typical substituents providing substituted polymers include halogens such as fluorine, chlorine and bromine; hydroxyl groups; lower alkyl groups; lower alkoxy groups; monocyclic aryl; lower acyl groups and the like.

Selection of the separation membrane for the present multicomponent membrane for gas separations is made on the basis of the heat resistance, solvent resistance, and mechanical strength of the separation membrane, as well as other factors dictated by the operating conditions for selective permeation, as long as the coating and separation membrane have the prerequisite relative separation factors in accordance with the invention for at least one pair of gases. The separation membrane is preferably at least partially self-supporting, and in some instances may be essentially self-supporting. The separation membrane may provide essentially all of the structural support for the membrane, or the multicomponent membrane may include a structural support member which can provide little, if any, resistance to the passage of gases.

The presently preferred multicomponent membranes are prepared from the polysulfones as described in U.S. Pat. No. 4,230,463 column 15 ff, particularly in the sturdy most useful form of coated hollow fibers, using polydimethyl siloxane or other similar silicone rubber coatings as described at column 19 line 42 ff. and in the Examples.

Methods of Reinjection

Methods of return 2 of the reject gas 3 to the main line 1, 4 of FIG. 1 can be as convenient and effective. Normally, reinjection of the reject gas stream to the main sour gas or field gas line is back into the suction side of the gas compressor. A venturi provides a convenient means, utilizing the pressure field gas pressure as driving force into the venturi, and injecting the reject gas into the throat of the venturi, utilizing the low pressure side of the compressor suction to "draw" the combined gas on into the compressor suction. See 2a of FIG. 2.

An alternative mode, 2c of FIG. 4, involves the use of a vacuum pump, which desirably can operate off the engine drive, to pull the reject gas from the membrane to form a reject stream and pump it into the low pressure field gas on the suction side of the compressor.

Another alternate means, shown in 2b of FIG. 3, uses an ejector or eductor. In this mode, a small side stream of high pressure gas can be utilized to drive the eductor or ejector, thus pulling the reject gas and producing a combined stream for injection into the suction side of the compressor.

EXAMPLES

The Example following is included to assist those skilled in the art with a further understanding of the invention. Particular streams, components, relationships, and the like, should be considered as illustrative and not limitative of the reasonable scope of my invention.

Example I

As a typical example, the inlet gas contained 79 percent methane and 21 percent other components including about 1 percent hydrogen sulfide. This field gas stream was readily converted to improve the motor octane number and reduce the hydrogen sulfide in accordance with my invention.

Employed was a commercial silicone polycarbonate membrane of 0.27 microns (0.0106 mil) thickness (MEM-213 from General Electric Co.). The effective exposed area of the membrane was 19 cm². The field gas was applied using inlet side pressure $P_i = 100$ psia, reject side pressure $P_f = 10$ psia, flow rate of upgraded gas $f_o = 475$ cc/min, and employing countercurrent flow as the method of reject gas withdrawal.

Results are shown in Table V:

TABLE V

Values for Natural Gas Components Relative to $H_2S$ in Offgas

| Component | $C_i^a$ | $C_o^a$ | $C_o/C_i$ |
|---|---|---|---|
| $CH_4$ | 78.998 | 89.00$^d$ | |
| $C_2H_6$ | 7.451 | 3.84$^b$ | 0.515$^m$ |
| $C_3H_8$ | 3.206 | 1.07$^b$ | 0.335$^m$ |
| i-$C_4H_{10}$ | 1.163 | 0.23 | 0.20$^e$ |
| n-$C_4H_{10}$ | 1.384 | 0.17 | 0.12$^e$ |
| i-$C_5H_{12}$ | 0.942 | 0.06 | 0.06$^e$ |

TABLE V-continued

Values for Natural Gas Components Relative to $H_2S$ in Offgas

| Component | $C_i^a$ | $C_o^a$ | $C_o/C_i$ |
|---|---|---|---|
| n-$C_5H_{12}$ | 0.531 | 0.01 | 0.025$^e$ |
| $C_6$ | 0.483 | 0.05 | 0.11$^e$ |
| $C_{7+}$ | 0.253 | 0.03 | 0.12$^e$ |
| $CO_2$ | 1.198 | 0.42$^b$ | 0.35$^m$ |
| $N_2$ | 3.341 | 5.01 | 1.50$^e$ |
| $H_2S$ | 1.050 | 0.105$^b$ | 0.100$^m$ |
| Calculated Btu content | Higher heating value | 1196 | 1014 |
| Calculated Btu content | Lower heating value | 1084 | 915 |
| Calculated Motor Octane Number | | 115.2 | 118.7 |

$^a C_i$ = concentration in inlet gas, mole %; $C_o$ = concentration in off-gas, mole %.
$^b$Calculated membrane offgas composition from curves in FIG. V.
$^d$Calculated by difference.
$^e$Calculated from relative permeabilities shown in Table VI.
$^m$Determined from measured $C_i$ and use of curves in FIG. 5.

TABLE VI

Selected Gas Permeabilities
( )* in a Silicone Polycarbonate Film

| Gas | Permeabilities |
|---|---|
| $N_2$ | 7 |
| $CO_2$ | 97 |
| $H_2O$ | 1000 |
| $H_2S$ | 280 |
| $CH_4$ | 27 |
| $C_2H_6$ | 70 |
| $C_3H_8$ | 113 |
| n-$C_4H_{10}$ | 250 |
| n-$C_5H_{12}$ | 557 |
| n-$C_6H_{14}$ | 262 |
| n-$C_8H_{18}$ | 238 |
| n-$C_{10}H_{22}$ | 120 |
| $C_6 \times nC_6$ | 262 |
| $C_7^+ = \frac{1}{2}(nC_6 + nC_8)$ | 250 |

*Units are: $10^{-9} \left( \frac{\text{cc of gas}}{\text{sec}} \right) \left( \frac{\text{(cm thick)}}{\text{(cm}^2\text{) (cm Hg } \Delta P)} \right)$;

alternatively: $4 \times 10^{-6} \left( \frac{\text{ft}^3 \text{ of gas}}{\text{min}} \right) \left( \frac{\text{(mil thick)}}{\text{(ft}^2\text{) (psi } \Delta P)} \right)$ i-$C_4H_{10} = \frac{1}{2}(nC_3 + nC_4)$
i-$C_5H_{12} = \frac{1}{2}(nC_4 + nC_5)$.

The data in Table V above illustrate the 90% reduction in $H_2S$ and the sharp reduction in $C_2$-$C_6$ hydrocarbons (with a corresponding increase in octane value) that are obtainable by my invention in upgrading field gas.

Example II

This example shows the permeabilities (P/l) for a number of gases through a multicomponent membrane utilizing a hollow fiber polysulfone porous separation membrane. The ratio of any two P/l values defines an approximate separation factor for those gases through the multicomponent membrane. This example shows that a multicomponent membrane may be used to separate any of a number of gases from each other. For example, from the table it is seen that $NH_3$ could be readily separated from $H_2$ or $N_2$, He from $CH_4$, $N_2O$ from $N_2$, $O_2$ from $N_2$, or $H_2S$ from $CH_4$, using this multicomponent membrane. The advantage of high permeation rates of the multicomponent membranes is indicated by the data represented in Table VII.

TABLE VII

Permeabilities[a] Of Fixed Gases Through A Multicomponent Membrane Utilizing Polysulfone Porous Separation Membrane[b]

| Gas | Multicomponent Membrane[b] $P/l (\times 10^6)$[a] |
|---|---|
| $NH_3$ | 210 |
| $H_2$ | 55 |
| He | 55 |
| $N_2O$ | 45 |
| $CO_2$ | 38 |
| $H_2S$ | 31 |
| $O_2$ | 8.3 |
| Ar | 3.3 |
| $CH_4$ | 2.3 |
| CO | 2.4 |
| $N_2$ | 1.4 |
| $C_2H_4$ | 1.7 |

[a] Permeabilities for the multicomponent membrane are P/l values and have units of cc(STP)/cm$^2$-sec cmHg.
[b] The multicomponent membrane in this example is comprised of a Dow Sylgard 184 post-vulcanized silicone rubber coated on a porous polysulfone separation membrane.

As a further illustration of the utility of the Prism membranes in separating $H_2S$ from other gases, reference is made to an article by E. A. Maciula, *Hydrocarbon Processing*, May 1980 p. 116.

The disclosure, including data, has illustrated the value and effectiveness of my invention. The examples, the knowledge and background of the field of the invention and general principles of applicable sciences, have formed the bases from which the description of the invention have been developed, and have formed the bases for my claims here appended.

I claim:

1. A method of protecting a natural-gas-utilizing engine from corrosion and knock which comprises the steps of:

treating a portion of a high pressure field gas stream containing primarily methane in admixture with hydrogen sulfide and/or higher hydrocarbons with a permeable membrane, wherein said membrane is relatively more permeable to said hydrogen sulfide and said higher hydrocarbons, thereby producing a reject gas stream enriched in hydrogen sulfide and/or higher hydrocarbons, and an off-gas useful as an upgraded fuel gas stream relatively depleted in hydrogen sulfide and/or higher hydrocarbons, reinjecting said reject gas stream to said low pressure field gas, and operating said gas-utilizing engine on said upgraded fuel gas.

2. The process according to claim 1 wherein said field gas comprises at least about 70% methane, and said upgraded fuel gas comprises at least about 85% methane.

3. The process according to claim 1 wherein field gas contains about 1 wt. % hydrogen sulfide, and said upgraded fuel gas contains about 0.1 wt. % hydrogen sulfide.

4. The process according to claim 1 wherein said reinjecting is accomplished by means of venturi on said low pressure gas line, by means of vacuum pump, or by means of an eductor.

5. The process according to claim 4 wherein said permeable membrane is a dimethyl silicone membrane.

6. The process according to claim 4 wherein said membrane is a silicone polycarbonate membrane.

7. The process according to claim 4 wherein said membrane is a polysulfone with a poly(alkylsiloxane) coating.

8. The process according to claim 7 employing said membrane as a hollow tube.

9. The process according to claim 4 wherein said high pressure field gas stream is produced by compressor means, having a low pressure inlet means and a high pressure discharge means, comprising a low pressure field gas stream; and said reinjecting of said reject gas stream is into said low pressure inlet means.

* * * * *